United States Patent [19]

Harandi et al.

[11] Patent Number: 4,830,635

[45] Date of Patent: May 16, 1989

[54] PRODUCTION OF LIQUID HYDROCARBON AND ETHER MIXTURES

[75] Inventors: Mohsen N. Harandi, Lawrenceville; Hartley Owen, Belle Mead, both of N.J.

[73] Assignee: Mobil Oil Corporation, New York, N.Y.

[21] Appl. No.: 130,259

[22] Filed: Dec. 8, 1987

[51] Int. Cl.$^4$ ............................................. C10L 1/02
[52] U.S. Cl. .......................................... 44/56; 44/53; 44/77; 502/159; 568/697; 585/415; 585/639
[58] Field of Search ............... 44/53, 56, 77; 568/697; 585/568, 415; 502/159

[56] References Cited

U.S. PATENT DOCUMENTS

| | | | |
|---|---|---|---|
| 3,846,088 | 11/1974 | Brown et al. | 44/56 |
| 3,849,082 | 11/1974 | Kozlowski et al. | 44/56 |
| 3,902,870 | 9/1975 | Rollmann et al. | 44/56 |
| 3,912,463 | 10/1975 | Kozlowski et al. | 44/56 |
| 3,960,978 | 6/1976 | Givins et al. | 260/683.15 R |
| 4,064,675 | 5/1987 | Torck et al. | 44/56 |
| 4,334,890 | 6/1982 | Kochar et al. | 44/53 |
| 4,433,185 | 2/1984 | Tabak | 585/312 |
| 4,456,779 | 6/1984 | Owen et al. | 585/415 |
| 4,544,776 | 10/1985 | Osterburg et al. | 568/697 |
| 4,554,386 | 3/1985 | Groeneveld et al. | 568/697 |
| 4,603,225 | 7/1986 | Colaianne et al. | 568/697 |
| 4,613,721 | 9/1986 | Kaiser | 585/643 |
| 4,647,703 | 3/1987 | Torck | 44/56 |
| 4,665,237 | 5/1987 | Arakawa et al. | 568/697 |
| 4,684,757 | 8/1987 | Avidan et al. | 585/331 |

FOREIGN PATENT DOCUMENTS 0026041 4/1981 European Pat. Off. .

OTHER PUBLICATIONS

U.S. Ser. No. 130,256, filed Dec. 8, 1987.
U.S. Ser. No. 130,258, filed Dec. 8, 1987.
U.S. Ser. No. 130,259, filed Dec. 8, 1987.
U.S. Ser. No. 130,260, filed Dec. 8, 1987.
U.S. Ser. No. 130,261, filed Dec. 8, 1987.

*Primary Examiner*—William R. Dixon, Jr.
*Assistant Examiner*—Margaret B. Medley
*Attorney, Agent, or Firm*—Alexander J. McKillop; Charles J. Speciale; L. G. Wise

[57] ABSTRACT

An etherification process for reacting a hydrocarbon mixture containing $C_4$–$C_7$ iso-olefins with excess methanol to produce tertiary alkyl methyl ethers. The improved technique comprises operations for separating etherification reaction effluent to recover a liquid fraction rich in gasoline range unreacted hydrocarbons in mixture with liquid ether product, recovering from the reaction effluent a vapor fraction rich in unreacted light olefin including $C_4$–$C_5$ olefins and unreacted methanol, and converting or interconverting a major portion of the light olefin to $C_4+$ olefins and/or oligomerization products while substantially completely converting the unreacted methanol to an acid zeolite catalysis conversion product comprising olefins and normally liquid hydrocarbon product. A portion of the conversion product is recycled to the etherification process.

28 Claims, 4 Drawing Sheets

PRODUCTION OF LIQUID HYDROCARBON AND ETHER MIXTURES

BACKGROUND OF THE INVENTION

This invention relates to processes for converting methanol and olefins to high octane liquid fuel. In particular, this invention relates to an integrated system for the production of methyl tertiary alkyl ethers in conjunction with the conversion of oxygenates and olefins to gasoline and distillate fuels.

In recent years, a major technical challenge presented to the petroleum refining industry has been the requirement to establish alternate processes for manufacturing high octane gasoline in view of the regulated requirement to eliminate lead additives as octane enhancers as well as the development of more efficient, higher compression ratio gasoline engines requiring higher octane fuel. To meet these requirements the industry has developed non-lead octane boosters and has reformulated high octane gasoline to incorporate an increased fraction of aromatics. While these and other approaches will fully meet the technical requirements of regulations requiring elimination of gasoline lead additives and allow the industry to meet the burgeoning market demand for high octane gasoline, the economic impact on the cost of gasoline is significant. Accordingly, workers in the field have intensified their effort to discover new processes to manufacture the gasoline products required by the market place. One important focus of that research is new processes to produce high octane gasolines blended with lower aliphatic alkyl ethers as octane boosters and supplementary fuels. $C_5$-$C_7$ methyl alkyl ethers, especially methyl tertiary butyl ether (MTBE) and tertiary amyl methyl ether (TAME) have been found particularly useful for enhancing gasoline octane. Therefore, improvements to the processes related to the production of these ethers are matters of high importance and substantial challenge to research workers in the petroleum refining arts.

It is known that isobutylene may be reacted with methanol over an acidic catalyst to provide methyl tertiary butyl ether (MTBE) and isoamylenes may be reacted with methanol over an acidic catalyst to produce tertiary-amyl methyl ether (TAME). In these etherification processes a problem of major importance is the separation of methanol from the etherification reaction product due to the proclivity of methanol to form a very dilute azeotropic mixture with hydrocarbons and the strong solubility of methanol in both water and hydrocarbons. Due largely to these factors, the cost associated with methanol separation and recycling in the etherification reaction represents approximately 30% of the cost of the total etherification process.

In U.S. Pat. No. 4,684,757 to Avidan et al. the well-known ability of zeolite type catalyst to convert methanol to olefins is utilized by directing unreacted methanol from an etherification reaction to a zeolite catalyzed conversion reaction for conversion to olefin, thereby obviating the need to separate and recycle methanol in the etherification reaction. However, the process of Avidan et al. converts oxygenate feedstock. The process incorporates an alkylation step in one embodiment to produce alkylate as well as $C_5+$ gasoline and $C_5+$ ethers.

The process for the conversion of methanol to olefins utilized in the Avidan et al. patent is but one in a series of analogous processes based upon the catalytic capabilities of zeolites. Depending on various conditions of space velocity, temperature and pressure methanol, and lower oxygenates in general, can be converted in the presence of zeolite type catalyst to olefins which may then oligomerize to provide gasoline or distillate or be converted further to produce aromatics.

In another application of zeolite catalysis, at low pressure and high temperature light olefins can be interconverted or redistributed to produce higher olefins rich in isoalkenes.

The feasibility and adaptability of the basic chemistry of zeolite oxygenates conversion to produce useful conversion processes has been the subject of much inventive research activity. Recent developments in zeolite catalyst and hydrocarbon conversion processes have created interest in using olefinic feedstocks for producing $C_5+$ gasoline, diesel fuel, etc. In addition to the basic work derived from ZSM-5 type zeolite catalyst, a number of discoveries have contributed to the development of a new industrial process, known as Mobil Olefins to Gasoline/Distillate ("MOGD"). This process has significance as a safe, environmentally acceptable technique for utilizing feedstocks that contain lower olefins, especially $C_2$-$C_5$ alkenes. In U.S. Pat. Nos. 3,960,978 and 4,021,502, Plank Rosinski and Givens disclose conversion of $C_2$-$C_5$ olefins, alone or in admixture with paraffinic components into higher hydrocarbons over crystalline zeolites having controlled acidity. Garwood et al. have also contributed improved processing techniques to the MOGD system as in U.S. Pat. Nos. 4,150,062, 4,211,640 and 4,227,992. The conversion of olefins to gasoline using a fluidized catalyst bed is the subject of U.S. Pat. application Ser. No. 6,407 to Owen, et al. The above identified disclosures are incorporated herein by reference.

The MOGD process may produce low octane gasoline. This disadvantage requires further downstream processing of the product so produced in order to provide a gasoline product with useful road octane value. Improvement of the process to provide an instant higher octane value gasoline product has been a much sought after objective in that field of art.

Recognizing the limiting problems of the etherification processes to produce MTBE and TAME and the potential that resides in the general area of the chemistry of oxygenate and olefin conversion with zeolites to resolve those problems, several objectives of the instant invention have been established.

First, it is an object of the present invention to provide an integrated process for the production of liquid fuel mixtures from olefin containing feedstock and lower alkyl alcohols by etherification and olefin conversion and interconversion reactions.

It is another object of the present invention to provide a process for the production of liquid fuels of enhanced octane value containing MTBE and TAME.

A further object of the instant invention is an integrated liquid fuels process wherein the etherification reaction is conducted with excess alcohol but which eliminates the need to recycle excess alcohol in the etherification reactor.

Yet another object of the instant invention is to provide an integrated liquid fuels production process wherein excess alcohol and olefins are converted to an isoalkene rich etherification recycle stream.

A further object of the present invention is to provide a liquid hydrocarbon integrated process incorporating etherification with oxygenates and olefin conversion wherein valuable isoalkenes in hydrocarbon feedstream are etherified prior to the conversion reaction.

SUMMARY OF THE INVENTION

In the production of ether-enhanced liquid fuels, it has been discovered that light olefin streams containing iso-olefins, such as isobutylene and isoamylene may be partially etherified with methanol or the like to produce lower alkyl tertiary alkyl ethers, with a novel recovery and conversion technique for the unreacted alcohol and light olefins from the etherification reaction effluent. By employing the versatile catalysis characteristics of acid zeolites, especially the medium pore metallosilicates such as HZSM-5, the excess methanol, or other lower alcohol, is converted to hydrocarbon concurrently with upgrading of the lower olefins.

This integration or coprocessing technique can eliminate a significant amount of downstream separation usually associated with the production of MTBE, TAME and other tertiary alkyl ethers. Separation and recovery steps for unreacted alcohol are eliminated by coconversion with light olefinic components of the etherification effluent and the product gasoline from the integrated process is rich in octane enhancing ethers.

In the integrated process of the present invention, the catalytic versatility of acid zeolites has been utilized employing conditions for the simultaneous conversion of lower alcohols to olefins and further oligomerization to useful gasoline fraction and distillate liquid with concomitant production of isoalkenes. The zeolite catalyzed olefin reactions also lead to valuable interconversion of lower olefins. The interconversion reaction leads to yet a further enhancement in the yield of isoalkenes, which can be recycled as a feedstream to the etherification reaction.

Accordingly, the invention provides an integrated process for the production of ether-rich liquid fuels, comprising; etherifying a mixture of excess lower alkyl alcohol and aliphatic hydrocarbon feedstock rich in $C_4+$ isoalkenes in the presence of an etherification catalyst whereby lower alkyl tertiary alkyl ethers are produced; separating the etherification effluent to provide a gasoline stream rich in $C_5+$ ethers and a stream comprising unreacted alcohol and alkenes; contacting said unreacted alcohol and alkenes with an acidic metallosilicate conversion catalyst under olefinic and oxygenates conversion conditions whereby a conversion effluent stream rich in $C_4+$ isoalkenes is produced; recycling at least a portion of said conversion effluent stream to the etherification mixture for further etherification.

In one embodiment of the present invention the etherification conditions comprise a high stoichiometric excess of lower alkyl alcohol over isoalkenes to shift the equilibrium of the etherification reaction substantially toward the formation of ethers.

Advantageously, the integrated process is employed whereby the isoalkene reactant in the etherification step is a mixture of $C_4$-$C_7$ iso-olefins and the ethers are recovered from the etherification reaction effluent in a product stream comprising gasoline range hydrocarbons.

DETAILED DESCRIPTION OF THE INVENTION

Figure 1:
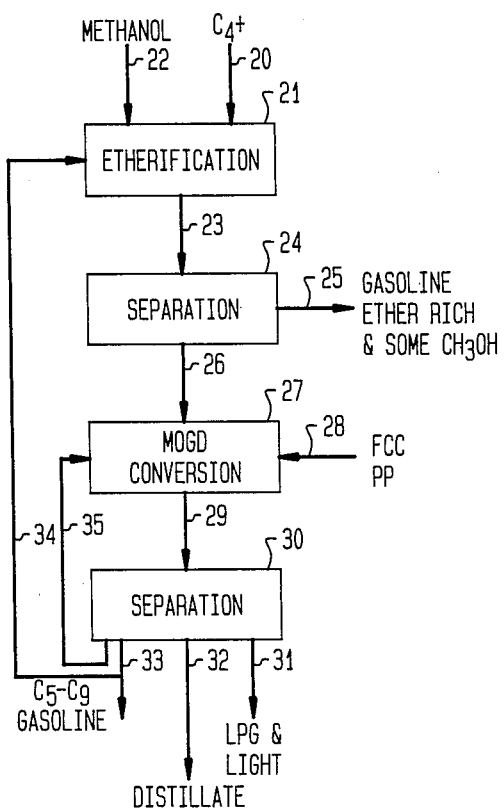
FIG. 1 of the drawings is a schematic flow diagram representing the major unit operations and flow streams of the invention incorporating MOGD conversion.

In the preferred embodiments of this invention methanol is reacted with a hydrocarbon feedstock containing olefins and particularly iso-olefins such as isobutene to produce methyl tertiary butyl ethers and other ethers.

Methanol may be readily obtained from coal by gasification to synthesis gas and conversion of the synthesis gas to methanol by well-established industrial processes. As an alternative, the methanol may be obtained from natural gas by other conventional processes, such as steam reforming or partial oxidation to make the intermediate syngas. Crude methanol from such processes usually contains a significant amount of water, usually in the range of 4 to 20 wt %. The etherification catalyst employed is preferably an ion exchange resin in the hydrogen form; however, any suitable acidic catalyst may be employed. Varying degrees of success are obtained with acidic solid catalysts; such as, sulfonic acid resins, phosphoric acid modified kieselguhr, silica alumina and acid zeolites. Typical hydrocarbon feedstock materials for etherification reactions include olefinic streams, such as FCC light naphtha and butenes rich in iso-olefins. These aliphatic streams are produced in petroleum refineries by catalytic cracking of gas oil or the like.

The major reaction units are operatively connected in a synergistic combination whereby etherification reaction effluent is utilized to provide additional reactive tertiary olefins by zeolite catalysis to provide olefin interconversion and oxygenate conversion. Isomerization, polymerization/oligomerization, alkylation and cracking reactions may be controlled in the acid catalysis zone to obtain a desirable distribution of normally liquid hydrocarbons useful in making gasoline and distillate range fuels. Advantageously, at least a portion of the gasoline range hydrocarbons are recovered with $C_5+$ etherate octane enhancers useful in quality motor fuels. MTBE and TAME are preferred etherates.

Etherification Operation

The reaction of methanol with isobutylene and isoamylenes at moderate conditions with a resin catalyst is known technology, as provided by R. W. Reynolds, et al., *The Oil and Gas Journal*, June 16, 1975, and S. Pecci and T. Floris, *Hydrocarbon Processing*, December 1977. An article entitled "MTBE and TAME—A Good Octane Boosting Combo," by J. D. Chase, et al., *The Oil and Gas Journal*, Apr. 9, 1979, pages 149-152, discusses the technology. A preferred catalyst is a bifunctional ion exchange resin which etherifies and isomerizes the reactant streams. A typical acid catalyst is Amberlyst 15 sulfonic acid resin.

MTBE and TAME are known to be high octane ethers. The article by J. D. Chase, et al., *Oil and Gas Journal*, Apr. 9, 1979, discusses the advantages one can achieve by using these materials to enhance gasoline octane. The octane blending number of MTBE when 10% is added to a base fuel (R+O=91) is about 120. For a fuel with a low motor rating (M+O=83) octane, the blending value of MTBE at the 10% level is about 103. On the other hand, for an (R+O) of 95 octane fuel, the blending value of 10% MTBE is about 114.

Processes for producing and recovering MTBE and other methyl tertiary alkyl ethers from $C_4$–$C_7$ iso-olefeins are known to those skilled in the art, such as disclosed in U.S. Pat. Nos. 4,544,776 (Osterburg, et al.) and 4,603,225 (Colaianne et al.). Various suitable extraction and distillation techniques are known for recovering ether and hydrocarbon streams from etherification effluent.

Operating details for typical MOGD units are disclosed in U.S. Pat. Nos. 4,456,779; 4,497,968 (Owen et al.) and 4,433,185 (Tabak), incorporated herein by reference.

In the process for catalytic conversion of olefins to heavier hydrocarbons by catalytic oligomerization using an acid crystalline zeolite, such as ZSM-5 type catalyst, process conditions can be varied to favor the formation of either gasoline, distillate or lube range products. At moderate temperature and relatively high pressure, the conversion conditions favor distillate range product having a normal boiling point of at least 165° C. (330° F). Lower olefinic feedstocks containing $C_2$–$C_5$ alkenes may be converted selectively; however, the low severity distillate mode conditions cannot completely convert the fraction of ethene in the feed. Propene, butenes and others may be converted to the extent of 99% per pass in the distillate mode.

In one preferred embodiment of the present invention, the alkene and unreacted alcohol fraction of the etherification reaction effluent is passed to an olefins interconversion reactor in contact with zeolite type catalyst such as ZSM-5. In the aforenoted MOGD process, light olefins are oligomerized to high molecular weight distillate range olefins over ZSM-5. In that process olefin molecular weight growth through a sequence of oligomerization and cracking reactions is thermodynamically forced at relatively high pressures of about 5600 kPa (800 psia) and relatively low temperatures of about 260° C. (500° F.). At much lower pressure and higher temperature, thermodynamics restrict the olefin distribution to low molecular weight. This is the basis for the olefin interconversion process, i.e., to operate under conditions where lower olefins, such as $C_2$–$C_4$ olefins can be converted to an equilibrium distribution of olefins with butenes and pentenes maximized. While providing redistribution or interconversion of olefins, it has been discovered that under such interconversion conditions lower oxygenates, such as methanol, are also converted to olefins in the presence of ZSM-5 catalyst when the reaction temperature is above 204° C. (400° F.). Accordingly, in the embodiment discussed herein, unreacted methanol from etherification is converted to olefins under conditions sufficient to distribute or interconvert lower olefins to an olefin stream rich in isobutene and tertiary pentenes. As a result, the unreacted methanol content of the etherification effluent stream can represent a high stoichiometric excess of methanol over isoalkenes in the etherification reaction. High excess methanol favorably shifts the equilibrium of the etherification reaction toward the formation of MTBE and TAME. In turn, excess methanol conversion to olefins with interconversion provides a recycle stream to the etherification process highly suitable for the production of the preferred lower alkyl tertiary alkyl ethers such as MTBE and TAME.

Utilizing the olefins interconversion reaction effluent stream as recycle to the etherification process provides further highly advantageous benefits in the separation of methanol in the effluent stream from the etherification reaction. Methanol forms an azeotropic mixture with hydrocarbons wherein methanol constitutes about 3% of the mixture. The olefin interconversion hydrocarbon recycle stream to the etherification reaction provides an added volume of hydrocarbons to separate methanol from the etherification reaction effluent as a feedstream to the olefin interconversion reaction operation.

The olefin interconversion process as utilized in the present invention can use fixed bed, moving bed or fluid bed reactors containing zeolite type catalysts such as ZSM-5. Operating conditions encompass temperatures between 200° C. (392° F.) and 400° C. (752° F.) and low pressures, generally between 100 and 500 kPa.

Referring now to FIG. 1, a schematic diagram of a preferred embodiment of the present invention is presented. Etherification hydrocarbon feedstream 20 preferably comprises prises a $C_4+$ hydrocarbon stream rich in isoalkenes. The hydrocarbon stream is passed to etherification reactor 21 and mixed with at least 2% excess of methanol based on the isoalkene content of the hydrocarbon stream. The etherification reaction is conducted preferably about 60° C. The etherification effluent is passed 23 to a fractionator 24 wherein a bottom stream 25 is separated comprising ether-rich gasoline. The overhead from the fractionator comprises essentially etherification excess methanol and all or a major portion of unreacted hydrocarbon. The mixture is passed to an olefins to gasoline and distillate conversion reactor 27 supplemented by a feedstream 28 of $C_3$ olefinic hydrocarbons. Olefins are converted to gasoline and distillate at a pressure between 4200 kPa and 7000 kPa (600 and 1,000 psia) and a temperature between 204° C. and 380° C. (400° and 600° F.). To convert olefins to gasoline, distillate, and lubes the MOGD operating pressure is increased above about 7000 kPa (1000 psia). The conversion effluent is passed 29 to a fractionation unit 30 for the separation of LPG and light hydrocarbons 31 distillate product 32 and a $C_5$–$C_9$ gasoline product 33. A portion of the $C_5$–$C_9$ gasoline product is recycled 34 to the etherification reactor. Preferably, the MOGD $C_5$ recycle is also sent to the etherification reactor and the recovered light hydrocarbon fraction contains unconverted normal alkenes plus $C_5$ recycle rich in alkenes. Optionally, in one preferred embodiment, a $C_6+$ fraction is separated 35 for recycle to the MOGD reactor.

Figure 2:
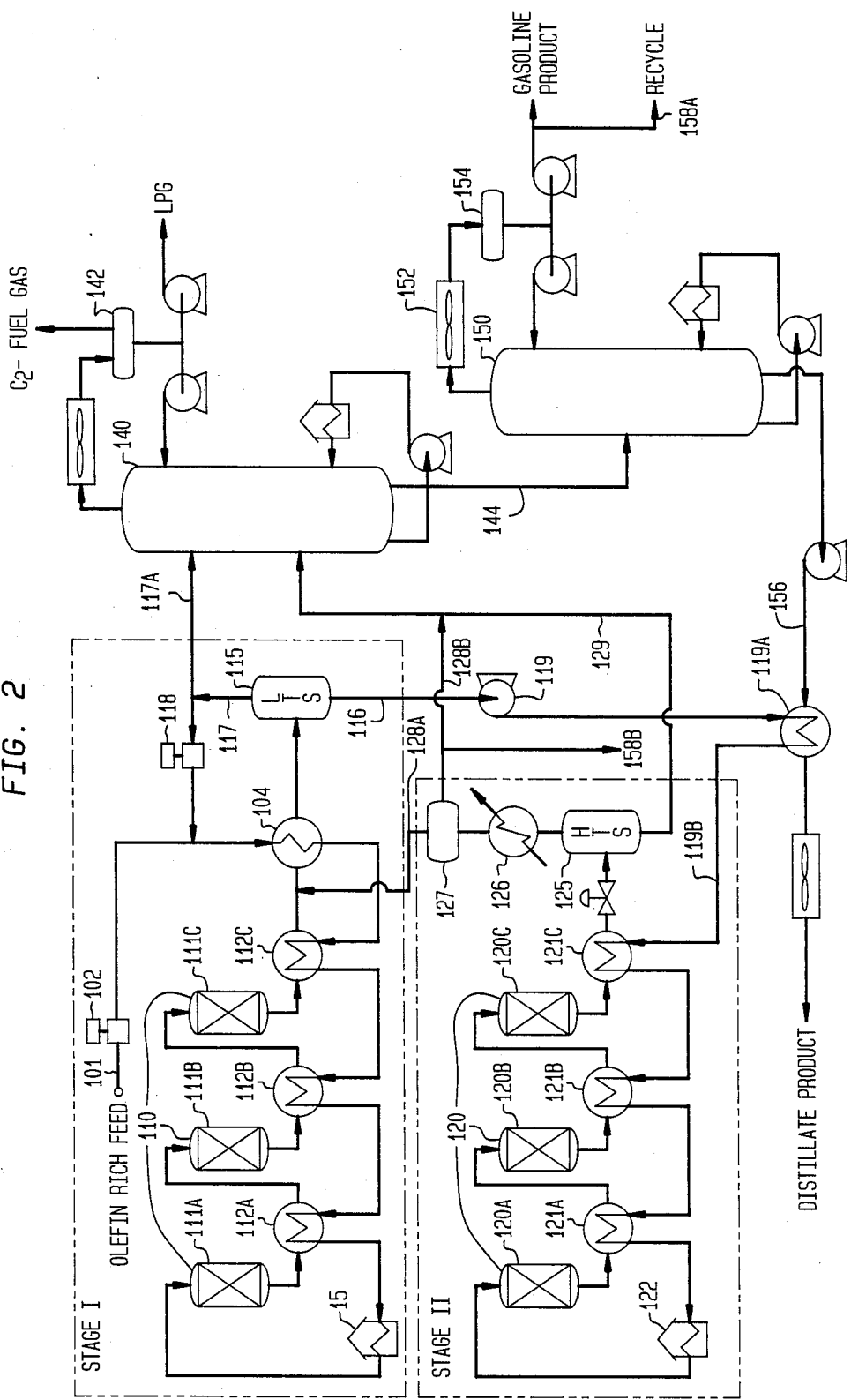
FIG. 2 is a more detailed process diagram of the oligomerization process for upgrading olefins.

Referring to FIG. 2, a detailed process flow diagram illustrates the primary olefin upgrade and oxygenates conversion process to gasoline and distillate that is incorporated as part of the integrated process of the present invention.

In stage 1 of FIG. 2, the reaction as employed herein refers to the combination of materials and conditions effective to convert lower olefins. This degree of reaction severity may be achieved by elevated temperature, catalyst activity, etc. in a known manner. In FIG. 2, unreacted methanol and butene-rich olefin are supplied to the olefins upgrading unit through fluid conduit 101 under steady stream conditions. This $C_3+$ feedstream is pressurized by compressor 102 and then sequentially heated by passing through process heat exchange units 104, 112, and furnace 105 to achieve the temperature for catalytic conversion in reactor system 110, including plural reactor vessels 111A, B, C. The reactor sub-system section shown consists of three downflow fixed bed, series reactors on line with heat exchanger cooling means 112 A, B, C between reactors and following the subsystem. The reactor configuration allows for any reactor to be in any position, A, B or C. The reactor in position A has the most aged catalyst and the reactor in position C has freshly regenerated catalyst. The cooled reactor effluent from exchanger 104 is first separated in a primary phase low temperature separator unit (LTS) 15 to provide a condensed $C_5+$ rich hydrocarbon liquid stream 16 and a primary light gas stream 117 comprising $C_2$-$C_4$ aliphatic hydrocarbons, along with ethane or other unreacted gaseous components which might be present in the feedstock, such as hydrogen, carbon oxides, methane, nitrogen or other inert gases. A major portion of this light gas stream is repressurized by compressor unit 118 for recycle wit fresh feedstock from compressor 102.

A typical severity multi-zone reactor system employs inter-zone cooling, whereby the reaction exotherm can be carefully controlled to prevent excessive temperature above the normal moderate range of about 260° to 370° C. Advantageously, the maximum temperature differential across any one reactor is about 30° C. and the space velocity (LHSV based on olefin feed) is about 0.5 to 1. Heat exchangers provide inter-reactor cooling and reduce the effluent to fractionation temperature. It is an important aspect of energy conservation to utilize at least a portion of the reactor exotherm heat value by exchanging hot reactor effluent from one or more reactors with a liquid stream to preheat the feed. Optional heat exchangers may recover heat from the effluent stream prior to fractionation. It is preferred to operate the high severity reactors at moderate pressure of about 1500 to 2900 kPa (200–400 psig), with a minimum olefin partial pressure of about 1200 kPa at the reactor system inlet.

The primary reactor system may contain multiple downflow adiabatic catalytic zones in each reactor vessel. The weight hourly space velocity (WHSV, based on total fresh feedstock) is about 0.1-2 LHSV. In this mode the molar recycle ratio for light gas is at least equimolar, based on total olefins in the fresh feedstock. The preferred molar ratio of recycle to fresh feedstock olefin is at least 2:1.

The secondary distillate production stage provides catalytic oligomerization reactor means containing medium pore shape selective zeolite oligomerization catalyst for converting lower and intermediate range olefinic hydrocarbons from the State I to liquid hydrocarbons comprising a major amount of distillate. Process stream 116, preferably comprising at least 75 mole % $C_5$ to $C_9$ aliphatic hydrocarbons, is pressurized for a substantially different process condition by pump means 19, operatively connected to provide a fluid handling system between Stages I and II. The intermediate liquid stream is preheated by indirect heat exchange with distillate product in exchanger 119A and passed to the Stage II subsystem at a pressure of at least about 4000 kPa, preferably about 4225 to 7000 kPa (600 to 1000 psig).

A typical distillate mode secondary stage reactor system 120 is depicted. A plural reactor system may be employed with inter-reactor cooling, whereby the reaction exotherm can be carefully controlled to prevent excessive temperature above the normal moderate range of about 190° C. to 315° C. (375°–600° F.). The olefinic intermediate stream comprising the $C_5+$ hydrocarbons is introduced through conduit 119B and carried by a series of conduits through heat exchangers 121A, B, C and furnace 122 where the intermediate stream is heated to reaction temperature. The olefinic stream is then carried sequentially through a series of zeolite beds 120A, B, C wherein a major portion of the olefin content is converted to heavier distillate constituents. Advantageously, the maximum temperature differential across the only one reactor is about 30° C. and the space velocity (LHSV based on olefin feed) is about 0.5 to 1.5. The heat exchangers 121A and 121B provide interreactor cooling and 121C further reduces the effluent. After flashing by mens of pressure reduction valve, the Stage II effluent is passed to secondary high temperature phase separator means 125.

This HTS unit is operated in a manner to recover the major amount of $C_{10}+$ hydrocarbons, while vaporizing at least a portion of light and intermediate ($C_5$-$C_9$) hydrocarbons at a pressure below 4000 kPa and temperature at least 100° C. higher than LTS unit 115. The $C_4$ and lighter components of this secondary vapor stream are recycled to Stage I via conduit 128A. Advantageously, at least a portion of the intermediate $C_5$-$C_9$ olefinic components are recovered by condensing the HTS vapor stream via exchanger 126 and separator 127. This condensed stream may be combined with other MOGD liquid via conduit 128B and fractionated for gasoline recovery and recycle to the etherification unit via conduits 158A and/or 158B. The HTS unit is operated at a pressure slightly above the Stage I effluent stream (e.g., about 3000 to 3500 kPa), with a recycle control system to maintain the desired pressure and flow rates.

Preferably, the secondary stage reactor conditions are optimized to produce heavy liquid hydrocarbons having a normal boiling above 165° C. (330° F). A typical secondary stage HZSM-5 fixed bed reactor system may be operated at about 0.5 to 2 liquid hourly space velocity (based on total olefins fed to reactors), temperature of 230° C. (450° F.) (SOC) to 315° C. (600° F.) (EOC) and a total pressure of 4225 kPa (600 psig), with a minimum olefin partial pressure at the inlet of about 1100 kPa (160 psig).

Product fractionation and optional recycle are achieved outside the recycle loops by passing a gas phase slip stream 117A and distillate-rich liquid stream 129 to a debutanizer tower 140 where $C_3$-$C_4$ LPG product is recovered from overhead condenser separator 142 and $C_2-$ of gas containing some unreacted ethane and a small amount of $C_4-$ hydrocarbons is recovered. The $C_5+$ liquid bottoms stream 144 is passed to product splitter tower 150 where $C_5$-$C_9$ raw gasoline product is recovered from the overhead condenser 152 and accumulator 154. A refined recycle stream can be drawn from the gasoline stream via conduit 158A to transfer to the etherification unit. Advantageously, the recycled intermediate hydrocarbons consist essentially of $C_5$ to $C_9$ aliphatics including at least 85 wt. % $C_5$ to $C_6$ iso-olefins. In a preferred embodiment, a $C_6+$ fraction is withdrawn 159 above inlet stream 144 for recycle to the MOGD unit.

The raw distillate product is recovered as a $C_{10}+$ bottoms stream via conduit 156 and exchanger 119A. Typical product fractionation systems are described in U.S. Pat. Nos. 4,456,779 and 4,504,693 (Owen et al.).

It is within the inventive concept to cascade a major amount of $C_5+$ hydrocarbons from the primary stage into the distillate mode reactor. This will optimize the process and will maximize distillate production by polymerizing gasoline boiling range components. Because the primary stage is operated at a pressure level of about 200–400 psig (1500–2900 kPa), the compression requirements are efficient. Also, common separators can be employed for both stages to effect preliminary product separation and provide recycle economically.

Table I presents a summarization of the overall effect of integrating the etherification process with olefins to gasoline and distillate conversion, based on Woerth LPG feed. Through the integration the gasoline plus distillate is increased by about 50 mol %. The combined process produced high quality distillate and gasolines representing an improvement over MOGD alone.

TABLE I

| Moles/Hr. | MOGD | MOGD/Ether. |
|---|---|---|
| $C_4^-$ | 109.81 | 107.11 |
| $C_5$ + gasoline | 21.57 | 5.30 |
| Ethers | — | 68.82 |
| Distillate | 58.82 | 46.67 |
| TOTAL | 190.20 | 227.90 |

In another preferred embodiment of the present invention, alkene containing hydrocarbon feed and methanol are first fed to an etherification reactor and unreacted methanol and lower olefins then fed to an olefin interconversion reactor. The components for etherification in the olefin interconversion reactor effluent are separated and recycled to the etherification reactor. The advantages of the proposed design are an elimination of the methanol recovery section of the etherification process and the conversion of the isoalkenes present in the feed to ethers upstream of the interconversion reactor; thereby avoiding oligomerization and cracking of valuable isoalkenes in the feed.

Figure 3:
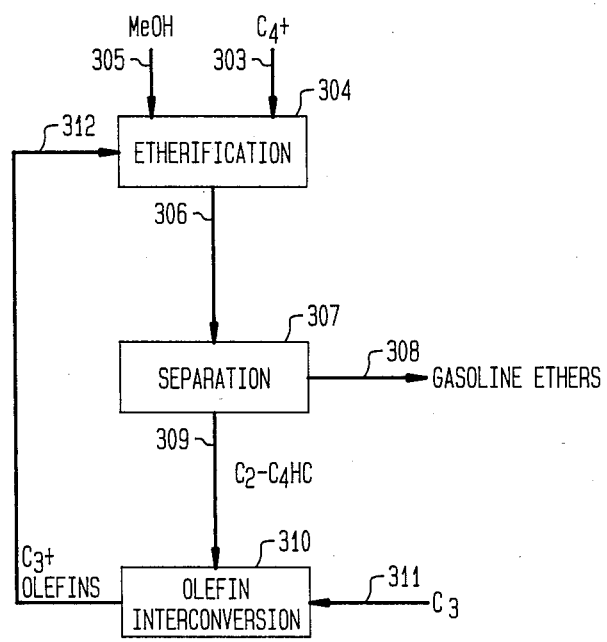
FIG. 3 is a schematic diagram of the embodiment of the present invention employing olefins interconversion and oxygenates conversion.

In FIG. 3 a schematic of a preferred integrated process of the instant invention is presented. A hydrocarbon feedstream containing $C_4+$ alkenes is passed 303 to etherification reactor 304 for etherification in the presence of about a 50% excess of methanol based upon the isoalkene content of the hydrocarbon feedstream. Methanol is passed to reactor 304 through conduit 305. Etherification reaction conditions are typical of those as described in the art heretofore and generally comprise a pressure of about 630 kPa (90 psi) and a temperature of about 60° C. in the presence of an etherification catalyst such as a sulfonic acid resin. The effluent 306 is separated in a fractionator 307 to provide an etherate rich gasoline stream 308 and an overhead stream of unreacted methanol and $C_5-$ hydrocarbons which is passed 309 to olefin interconversion reactor 310. The interconversion reaction is conducted in contact with zeolite type catalyst, such as ZSM-5, at a pressure of about 105 kPa (15 psi) and a temperature of about 276° C. (530° F). Typically, a supplemental propene-rich feedstream is passed 311 to the interconversion reactor where about 25% of the combined olefinic feed is converted to isoalkenes. The effluent from the reactor consisting of $C_3+$ hydrocarbons rich in isoalkenes is recycled 312 to etherification reactor.

Figure 4:
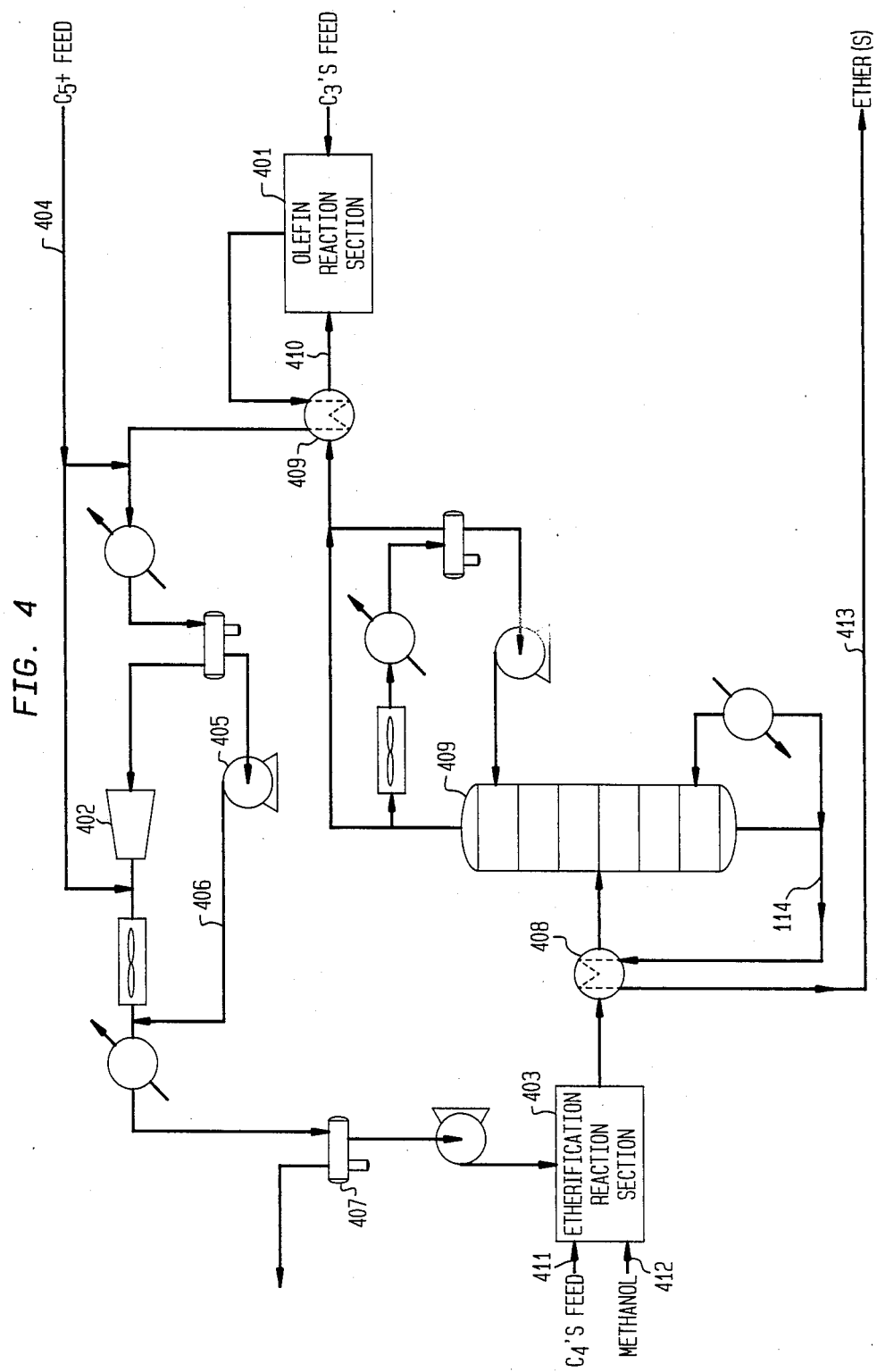
FIG. 4 is a more detailed flow diagram of the invention incorporating olefins interconversion.

In FIG. 4 a more detailed process flow diagram of the olefins interconversion embodiment of the instant invention is presented. In this embodiment the relatively low pressure effluent from the olefins interconversion reactor 401 is recompressed in compressor 402 before passing to etherification reactor 403. However, before recompression the effluent can be mixed with a $C_5+$ feedstream 404 which serves to augment the separation of liquid hydrocarbons which bypass the compressor through pump 405 in bypass loop 406. A portion of the effluent stream after compression is purged of paraffins in separator 407 before feeding to etherification reactor. After cooling of the etherification reactor effluent in cooler 408 by indirect heat transfer with debutanizer 409 bottoms, the debutanizer separated overhead is preheated by indirect heat transfer with reactor 401 effluent in heat exchanger 409 before passing 410 to the olefins interconversion reactor. The hydrocarbon feed 411 to etherification reactor is preferably rich in $C_4+$ isoalkenes and the methanol feed 412 can be a small or high stoichiometric excess based on isoalkenes in the feed. Ether rich gasoline is withdrawn as a bottom product from the debutanizer through conduit 413.

In the olefin interconversion process all types of olefins are selectively converted to $C_4+$ isoalkenes. The $C_4$ and $C_5$ yield increases as the olefins partial pressure is reduced. At an olefin partial pressure of about 2.9 psia the $C_4$ and $C_5$ olefin yield, based on propene conversion, is about 42%. The iso-olefins concentration in the $C_4$-$C_5$ olefins fraction is about 60%. In Table II below, a conventional etherification process, Column A is compared to the integrated etherification/olefins interconversion process of the present invention, Column B.

TABLE II

| | A<br>FCC $C_4$-$C_5$<br>Etherif. | B<br>FCC $C_3$-$C_5$<br>Etherif. + MOI |
|---|---|---|
| Total Olefins Conversion, wt % | 34 | 89 |
| $C_5$ + Debutanized Gasoline, MLBS/HR | 74 | 156 |
| MTBE, MLBS/HR | 23 | 41 |
| TAME, MLBS/HR | 19 | 34 |
| $C_7$ + Ethers, MLBS/HR | — | 10 |
| Estimated $C_5$ + Octane, R + O | 100 | 98 |

The high olefin conversion in the process of the instant invention is due to the high propane conversion in the olefin interconversion reactor (93%) and the process 6/1 recycle to hydrocarbon feed ratio in order to operate the interconversion reaction at about 2.9 psia olefin partial pressure. The recycle stream is highly paraffinic and contains more than 50% isobutane.

While the invention has been described by specific examples and embodiments, there is no intent to limit the inventive concept except as set forth in the following claims.

What is claimed is:

1. An integrated process for the production of ether-rich liquid fuels, comprising;
   (a) etherifying a mixture of excess lower alkyl alcohol and aliphatic hydrocarbon feedstock rich in $C_4+$ isoalkenes in the presence of acid etherification catalyst whereby lower alkyl tertiary alkyl ethers are produced;
   (b) separating etherification effluent from step (a) to provide a gasoline stream rich in $C_5+$ ethers and a stream comprising unreacted alcohol and alkenes;
   (c) contacting said unreacted alcohol and alkenes with an acidic metallosilicate zeolite conversion catalyst under olefinic and oxygenates conversion conditions at a temperature of at least 200° C. (392°

F.) whereby a conversion effluent stream rich in $C_{4+}$ isoalkenes is produced;

(d) recycling at least a portion of said conversion effluent stream to step (a) for etherification.

2. The process of claim 1 wherein said isoalkenes include isobutene; said lower alkyl alcohol includes methanol, said conversion catalyst comprises a shape selective medium pore acid metallosilicate zeolite; and said lower alkyl tertiary alkyl ethers contain tertiary butyl ether.

3. The process of claim 1 wherein the etherification catalyst comprises an acid sulfonic acid resin solid.

4. The process of claim 2 wherein the isoalkene reactant in step (a) is a mixture of $C_4$-$C_7$ tertiary olefins, and the lower alkyl tertiary alkyl ethers are recovered from the reaction effluent of step (a) in a product stream comprising gasoline range hydrocarbons.

5. The process of claim 4 wherein the lower alkyl tertiary alkyl ethers comprise $C_5$ to $C_8$ methyl tertiary alkyl ethers.

6. A process for the conversion of $C_{2+}$ alkene-rich feedstock to ether-rich gasoline, comprising the steps of:

(a) contacting a mixture comprising lower alkyl alcohols and a feedstock comprising a $C_{4+}$ olefin-rich aliphatic hydrocarbon stream with an acid etherification catalyst in an etherification zone under etherification conditions to produce an effluent stream comprising $C_{5+}$ lower alkyl tertiary alkyl ethers, unreacted alcohol and $C_{2+}$ aliphatic hydrocarbons;

(b) separating said effluent stream to produce an ether-rich gasoline stream and a stream comprising unreacted lower alkyl alcohol and $C_{4-}$ aliphatic hydrocarbons;

(c) contacting step (b) unreacted lower alkyl alcohol and said $C_{4-}$ aliphatic hydrocarbon stream with zeolite-type catalyst in a common conversion zone under conversion conditions suitable for olefinic interconversion and lower alkyl alcohol conversion to olefins whereby a conversion effluent stream comprising $C_{4+}$ isoalkenes-rich hydrocarbons is produced;

(d) recycling a portion of said conversion zone effluent stream to said etherification zone under etherification conditions whereby lower alkyl tertiary alkyl ethers are produced.

7. The process of claim 1 wherein the etherification conditions comprise a high stoichiometric excess amount of said lower alkyl alcohol over isoalkenes to shift the equilibrium of the etherification reaction substantially toward the formation of $C_{5+}$ ethers.

8. The process of claim 7 wherein the mole ratio of said lower alkyl alcohol to $C_{4+}$ isoalkenes is between 10:1 and 1:1.

9. The process of claim 7 wherein the mole ratio of said lower alkyl alcohol to $C_{4+}$ isoalkenes is preferably about 1.2:1.

10. The process according to claim 6 wherein step (b) effluent stream unreacted lower alkyl alcohol is between 1 to 20 weight percent of the $C_{5-}$ aliphatic hydrocarbon content of said stream.

11. The process of claim 6 wherein the lower alkyl alcohol comprises methanol.

12. The process of claim 6 wherein said lower alkyl tertiary alkyl ethers are taken from the group consisting essentially of ethers of the following formula:

$$R-O-R',$$

where R is methyl or ethyl and R' is taken from the tertiary alkyl isomer radicals of butane, pentane, hexane, heptane, octane and nonane.

13. The process of claim 12 wherein said ethers comprise methyl tertiary butyl ether and methyl tertiary amyl ether.

14. The process of claim 6, further comprising the steps of:

(a) passing $C_3$ alkene feedstock and inert components to the conversion zone for olefinic interconversion in contact with zeolite catalyst whereby $C_{4+}$ isoalkenes are produced;

(b) cooling and separating said conversion zone effluent stream to provide liquid and vapor streams and compressing the vaporous portion thereof;

(c) combining the liquid and compressed vapor streams containing $C_{4+}$ isoalkenes and inert components and passing the combined stream to the etherification zone to etherify said iso-alkenes.

15. The process of claim 6 wherein said zeolite-type catalyst comprises ZSM-5.

16. A process for producing liquid fuel mixtures from olefin feedstock and alkanol by multistage etherification and oligomerization reactions, comprising the steps of:

(a) reacting an olefin hydrocarbon feedstock mixture containing $C_{4+}$ isoalkene and n-alkenes with a stoichiometric excess of lower aliphatic alkanol in the presence of an acid etherification catalyst under reaction conditions effective to produce a mixture of tertiary alkyl ethers;

(b) recovering a light hydrocarbon fraction containing unreacted alkenes from the reaction effluent of step (a) along with unreacted alkanol;

(c) contacting the recovered light hydrocarbon and alkanol fraction from step (b) with an acid oligomerization and oxygenate conversion catalyst comprising shape selective medium pore acid metallosilicate zeolite to convert at least a portion of said unreacted n-alkenes and alkanol to heavier liquid hydrocarbon product, including $C_{10+}$ distillate range hydrocarbons and $C_5$-$C_9$ hydrocarbons rich in olefinic hydrocarbons containing isoalkenes and;

(d) recovering at least a portion of said intermediate olefinic hydrocarbons containing isoalkenes from the conversion effluent of step (c) for recycle to step (a) for further etherification reaction.

17. The process of claim 16 wherein said isoalkene includes isobutene, said alkanol includes methanol; and said tertiary alkyl ethers contain methyl t-butyl ether.

18. The process of claim 17 wherein the isoalkene reactant in step (a) is a mixture of $C_4$-$C_7$ iso-olefins, and the tertiary alkyl ethers are recovered from the reaction effluent of step (a) in a product stream comprising gasoline range hydrocarbons.

19. The process of claim 18 wherein the tertiary alkyl ethers comprise $C_5$ to $C_8$ methyl tertiary alkyl ethers.

20. The process of claim 16 wherein fresh olefinic feedstock is rich in butenes.

21. The process of claim 16 wherein the olefinic feedstock contains about 10 to 50 weight percent isobutylene.

22. The process of claim 16 including the further step of recovering the light hydrocarbon stream in step (b) by fractionating substantially the entire etherification reaction effluent in a debutanizer column to provide an overhead vapor stream rich in $C_{4-}$ lower olefin and containing a minor amount of excess unreacted methanol, and to provide a liquid product stream consisting essentially of $C_5+$ liquid hydrocarbon and $C_5+$ methyl tertiary alkyl ether.

23. The process of claim 16 wherein the etherification catalyst comprises an acid sulfonic acid resin solid.

24. The process of claim 19 wherein the olefinic feedstock comprises $C_5+$ isoalkene and the methyl tertiary alkyl ether comprises t-amyl methyl ether.

25. The process of claim 16 wherein fresh olefin feedstock consists essentially of a mixture of $C_3$–$C_7$ olefins.

26. The process of claim 16 wherein the recycled intermediate hydrocarbons in step (d) consist essentially of $C_5$ to $C_9$ aliphatics including at least 60 wt. % tertiary iso-olefins.

27. In the etherification process for reacting an olefinic hydrocarbon mixture containing $C_4$–$C_7$ iso-olefins with excess methanol to produce t-alkyl methyl ethers, the improvement which comprises:

separating etherification reaction effluent to recover a liquid fraction rich in gasoline range unreacted hydrocarbons in mixture with liquid ether product;

recovering from said reaction effluent a fraction rich in unreacted light olefin including $C_4$–$C_5$ olefins and unreacted methanol; and converting a major portion of said light olefin and substantially completely converting said unreacted methanol to an acid catalysis conversion product comprising a major amount of normally liquid hydrocarbon product.

28. The process of claim 16 wherein said metallosilicate zeolite comprises ZSM-5.

* * * * *

UNITED STATES PATENT AND TRADEMARK OFFICE
CERTIFICATE OF CORRECTION

PATENT NO. : 4,830,635

DATED : May 16, 1989

INVENTOR(S) : Mohsen N. Harandi et al.

It is certified that error appears in the above-identified patent and that said Letters Patent is hereby corrected as shown below:

Col. 5, line 5-6     "iso-olefeins" should be --iso-olefins--.
Col. 8, line 14     "mens" should be --means--.
Col. 11, Claim 9, line 57     delete "preferably".
Col. 11, Claim 10, line 61     "$C_5$-" should be --$C_4$--.

Signed and Sealed this

Twentieth Day of March, 1990

Attest:

JEFFREY M. SAMUELS

Attesting Officer     Acting Commissioner of Patents and Trademarks